United States Patent [19]

Krummenacher

[11] Patent Number: 5,340,729
[45] Date of Patent: Aug. 23, 1994

[54] METHOD FOR PRODUCING SPAGYRIC ESSENCES FROM PLANTS

[76] Inventor: Beat R. Krummenacher, Tägertschistr. 34a, CH-3110 Münsingen, Switzerland

[21] Appl. No.: 90,428

[22] Filed: Jul. 12, 1993

Related U.S. Application Data

[63] Continuation-in-part of Ser. No. 867,181, Jul. 9, 1992.

[30] Foreign Application Priority Data

Oct. 22, 1990 [CH] Switzerland ................ 3353/90

[51] Int. Cl.$^5$ .................. A61K 35/78; C12P 1/02; C12P 7/10
[52] U.S. Cl. .................... 435/171; 435/7.31; 435/41; 435/156; 435/161; 435/165
[58] Field of Search ............... 435/41, 161, 171, 7.31, 435/156, 165

[56] References Cited

U.S. PATENT DOCUMENTS 4,497,896 2/1985 Assarsson et al. .............. 435/161
4,578,353 3/1986 Assarsson et al. .............. 435/165

FOREIGN PATENT DOCUMENTS 1617314 2/1971 Fed. Rep. of Germany.
1539878 9/1969 France.

OTHER PUBLICATIONS

Patent Abstracts of Japan vol. 9, No. 228 (C-303) 1951 Sep. 13, 1985 (JP,A, 60-087 207) Iwasekenjirou Shiyouten KK May 16, 1985.

*Primary Examiner*—Herbert J. Lilling
*Attorney, Agent, or Firm*—Speckman, Pauley & Fejer

[57] ABSTRACT

A method for producing spagyric essences in the form of standardized products with defined alcohol contents in respect to the dried residue of plants used in said method. The components of a spagyric essence which are important from the spagyric point of view—fermentation alcohol, volatile aromatic substances and soluble mineral salts—are obtained totally and in pure form. The production process is distinguished by a way to prepare the yeast fermentation which prevents the development of undesirable micro-organisms, by gentle vacuum distillation, by complete incineration with exhaustive extraction of the mineral substances and by different methods for removing impurities which were also extracted. Spagyric essences or primary tinctures are used as medicaments in human and veterinary medicine.

13 Claims, No Drawings

METHOD FOR PRODUCING SPAGYRIC ESSENCES FROM PLANTS

CROSS REFERENCE TO RELATED APPLICATION

This application is a continuation-in-part of copending U.S. patent application having Ser. No. 867,181, filed Jul. 9, 1992.

BACKGROUND OF THE INVENTION

1. Field of the Invention

This invention relates to a method for producing spagyric essences from fresh or dried plants or parts of plants.

2. Description of Prior Art

Spagyric essences (in Latin "essentia"=the essential matter of a thing) are used as medicaments in connection with human and veterinary medicine. The methods for their production rest on the theoretical background of the alchemistic spagyria. They are, therefore, identified as spagyric production methods or spagyrics. Many written records in this field are known to exist, in particular from Paracelsus. The term spagyrics has been created by the combination of two Greek words: "span" which means to separate, to divide, and "ageirein" which means to bind, to unite. Thus, the word itself defines the typical aspect of the spagyric production method: the curative contents or principles of effectiveness of a basic substance are specifically liberated and are combined into medicaments by suitable repositioning. However, spagyrics extends further in it requirements than the modern, conventional preparation of medicaments. The latter is based on a direct correlation between the chemical substance and the effects. The substance itself causes the effects. For this reason, modern medicament production always tries to isolate or enrich individual active ingredients. Methods used in connection with this approach, in particular with plants, are maceration or extraction. Spagyrics does not make a direct connection between the physical material and the effects. Its understanding of medicaments is based on active principles not directly tied to substances. The substances are merely used as carriers of these active principles. In general, active principles are not tied to individual substances but rather are supported by entire groups of substances. It is assumed that the active principles are located in three components or groups of substances of the plant. These components are: the soluble mineral salts, the volatile aromatic substances and the alcohol generated in the course of fermentation of the raw substances. In accordance with spagyric teachings, these three components must be separately isolated by separation or division and then reunited in a suitable manner. To achieve this, the spagyric basic process consists of four steps:

1. Fermentation
2. Separation
3. Purification
4. Combination

The fermentation of organic components and subsequent distillation to obtain alcohol-containing liquids is a known method used in the most diverse fields. U.S. Pat. Nos. 4,497,896 and 4,578,353 disclose such methods for obtaining ethanol. However, the methods are not used for preparing medicaments.

Various methods are known which, as spagyrics, have as their goal the production of medicaments on a vegetable basis in such a way that the healing principles of the plants are obtained.

For example, German Patent Publication DE-A-16 17 314 discloses a method for obtaining wines with prophylactic properties from medicinal plants. The plants are fermented by the addition of water, glucose and yeast. Subsequently, the fermented liquid is separated from the solid components by screening and pressing. Renewed fermentation takes place after honey is added and benzoic acid is added for preservation. After filtration, a drinkable honey wine is produced.

French Patent Publication FR-A-1,539,878 discloses a method for the preparation of a primary tincture on a vegetable basis, wherein the plants are macerated and are subsequently fermented in distilled water. Then the plant residue is separated from the liquid by filtering and pressing. The plant residue is incinerated and the ash is added to the liquid so that the soluble mineral salts can be dissolved in it. Following another filtration, the solution obtained is subjected to light until a clear liquid is obtained.

Both methods have some basic features which correspond with the spagyric teachings. Although both employ fermentation at the start, only simple separation processes follow. However, this separation in accordance with the teachings of German Patent Publication DE-A-16 17 314 is incomplete because mineral substances are rejected together with the screened and pressed residue and are therefore lost. In addition, simple filtration cannot be compared with purification by distillation and reduction of the residue. Although French Patent Publication FR-A1,539,878 teaches isolation of the ash from the fermentation residue, the salts are not purified before being added to the filtrate. With both methods, the filtrate or the pressed matter itself is not subjected to purification processes.

Japanese Patent Publication JP-A-60,87207 discloses a method for obtaining a fermented extract from species of aloe (genus Aloe, Liliaceae family) for external application. In this method, too, the separation is incomplete, analogous to German Patent Publication DE-A-16 17 314.

SUMMARY OF THE INVENTION

It is, therefore, the object of this invention to provide a method for producing essences on a vegetable basis, which uses the theoretical principles of spagyrics, but satisfies the criteria of medicament production valid today. The method is intended to result in a predetermined amount of product with a predetermined alcohol content, i.e. it is to be standardized.

This object is obtained by a method for producing spagyric essences from fresh or dried plants or plant parts in which the dry basis of the plant used is determined, thereby providing a basis for determining the amount of end product desired, as well as the amount of an intermediate product of a first fraction of a distillation and the amount of carbohydrates required by the method to obtain the desired end product. The plant material is comminuted and mixed with fermentable carbohydrates dissolved in water and yeast. The resulting mixture is stirred, initially to at least cover the plant material with water, and thereafter at least once a day until the plant material is fermented, forming a fermented mass. The fermented mass is distilled in a vacuum, resulting in the collection of a first fraction containing all of the alcohol derived from the fermentation and a second fraction comprising the portion of the distillate remaining after collection of the first fraction. Alcohol is then added to the first fraction to provide between about 10% and about 80% of the alcohol of the end product. The distillation residue is dried, burned and completely incinerated at about 300° C. to about 700° C. to form an ash comprising at least one soluble mineral salt. The soluble mineral salt is extracted from the ash with a sorbent producing purified salt extracts which are recombined and dried while removing impurities therefrom. The dried salts are dissolved in a portion of said first fraction, and deposits which may be formed are filtered off. The resulting purified salt solution is mixed with the remaining portion of said first fraction to which a sufficient amount of the second fraction is added to produce the predetermined amount of end product.

The essential features of this method are yeast fermentation, gentle vacuum distillation, complete incineration of the entire distillation residue with exhaustive extraction of the soluble mineral salts from the ash, separation of dissolved impurities from the salt extracts and a combination of the distillate with the mineral salts in a clear solution with a predetermined alcohol content.

The method in accordance with this invention will be better understood from the following detailed description.

DESCRIPTION OF PREFERRED EMBODIMENTS

In accordance with one embodiment of the method of this invention, the essences are prepared preferably from fresh or, in exceptional cases, deep frozen or dried plants or plant parts. Examples of plants suitable for use in this method are: Valeriana officinalis, Ginkgo biloba, Panax ginseng or Amanita muscaria. First, the plants or plant parts are finely comminuted. The dry residue T, in percent, is determined from a sample. The nominal amount U of the primary tincture or essence is calculated from the total plant matter M in kilograms in accordance with the following formula:

$$U = 0.1 \cdot M \cdot T \text{ [kg]},$$

where the product of the total plant matter and the dry residue, M·T, results in the dry mass.

The amounts of water, carbohydrates, for example sucrose, and yeast required for the fermentation mix are determined in accordance with the following formulas:
Amount of water $W = U$ [kg]
Sucrose $S = 0.03 \cdot U$ [kg]
Yeast $H = 0.002 \cdot U$ [kg]

The entire amount of water is placed into a suitable mixing vessel and the sucrose is dissolved therein. Then the yeast is stirred in, after which the comminuted plant matter is mixed in. If the plant matter is not covered at least slightly with liquid, water should be added until it is covered.

The contents of the mixing vessel are left to ferment at a temperature of between about 15° C. to about 25° C. with daily thorough stirring and submersion of the solids which have risen to the top. As soon as the fermentation process has come to an end, the entire mass is distilled in vacuo. Two fractions are collected at a pressure of 135 mbar, wherein their nominal amounts are defined as follows:
Fraction $1 = F1 = 0.7 \cdot U$ [kg]
Fraction $2 = F2 = 0.15 \cdot U$ [kg]

The ethanol content A (weight percent) is determined in the effectively collected amount D of Fraction 1 which, with the exception of process-related fluctuations, agrees with the above defined amount F1. Then 94% ethanol (weight/weight) is added in the amount Z:

$$Z = (1/94) \cdot (22 \cdot U - A \cdot D) \text{ [kg]}$$

The predetermined amount of the Fraction 1 can only be attained approximately in actual use due to measuring errors when metering the Fraction 1, which in actuality cannot be avoided. For example, a change of the recipient for Fraction 1 which takes place just a little late results in a somewhat larger amount of collected Fraction 1 than theoretically required. For this reason, the effectively collected amount D is made the basis for calculating the ethanol to be added.

The distillation residue is dried, burned and completely incinerated at a temperature of 480° to 520° C. The soluble salts are exhaustively extracted from the ash with boiling water as the solvent. The salt extracts are filtered, recombined and dried. The purified salt is dissolved in a portion of the Fraction 1 mixed with alcohol which is sufficient for dissolving the salt. In the course of this, impurities can again be deposited and filtered off. The clear solution is mixed with the remainder of the alcoholic Fraction 1. Finally, a sufficient amount of the Fraction 2 is added to the mixture so that the total amount corresponds with the predetermined nominal amount U. The resulting liquid is the spagyric essence or the primary tincture of the plants used. The distillation residue is dried, burned and completely incinerated at a temperature of about 480° C. to about 520° C. The soluble salts are exhaustively extracted from the ash with boiling water as the solvent. The salt extracts are filtered, recombined and dried. The purified salt is dissolved in a portion of the Fraction i mixed with alcohol which is sufficient for dissolving the salt. In the course of this, impurities can again be deposited and filtered off. The clear solution is mixed with the remainder of the alcoholic Fraction 1. Finally, a sufficient amount of the Fraction 2 is added to the mixture so that the total amount corresponds with the predetermined nominal amount U. The resulting liquid is the spagyric essence or the primary tincture of the plants used.

This method contains several advantages:

The amount of the product is at a defined proportion to the dry mass of the plants, therefore this method is independent of the water content of the plants used. In the various examples disclosed, numerical factors are cited. These factors have proven effective for many types of plants. In the general case, however, the numerical factors are replaced by variables. The numerical values which are inserted into these variables are empirical values. However, the amount of end product desired can be predetermined in every case based upon the dry mass of the plant material being used.

By the addition of carbohydrates, a constant and high quality product of spagyric essences can be obtained. Plants with high water content or low carbohydrate proportions often ferment very little, fungi often appear or they may rot. But if carbohydrates, such as sucrose or honey, are added, strong fermentation takes place.

The plant matter is only added to the mixture of water, sucrose and yeast at the end. In this way, all plant parts are covered by a sufficiently dense yeast population. This permits a controllable yeast fermentation in that the yeast development is aided and growth of unwanted germs is prevented.

The fermentation temperature should be determined as a function of the yeast used, so that fermentation processes take place as optimally as possible. In this example, the fermentation temperature lies between about 15° C. and about 25° C. It is also necessary, for an optimal fermentation process, that the plants be covered with water. But because of the formation of carbon dioxide, a portion of the mass is pushed above the level of the liquid again and again. Therefore regular stirring and submersion of the solid particles assures that this general requirement is met. The end of fermentation is determined where no more fermentation gases, particularly carbon dioxide, are formed and the solid parts have sunk to the container bottom as a rule. The length of fermentation depends on the type of plants used, the type of yeast and the fermentation temperature. It can be from a few days to months.

Because vacuum distillation is employed, the temperature-sensitive aromatic substances obtained during fermentation do not decompose under these gentle conditions.

The distillate is collected in two fractions so that the condition of standardization can be met. Only in this way is it possible that the amount of the end product is in a fixed relationship to the dry mass of the initial plants used. The aromatic substances and the alcohol created by the fermentation process are mainly distilled out at the beginning and their proportion in the distillate becomes progressively less with continuing distillation. For this reason, the amount of intermediate product of the first fraction should be as large as possible, because it must contain all of the alcohol generated during fermentation. In spite of this, it, together with the later additions, is not permitted to exceed the amount of end product to be achieved. The second fraction is used for the exact definition of the amount of end product with a view to standardization and consists of the portion of the distillate which is obtained after the collection of the first fraction until the end of distillation. The second fraction can also additionally be used in obtaining the soluble mineral salts.

The alcohol content of the first fraction is determined so as to reach the set alcohol content of the nominal amount. From this, the amount of ethanol still to be added is determined by means of the above mentioned formula and taking into consideration the amount of alcohol contained in the first fraction. The alcohol content of the nominal amount of the essence lies between 10% and 80%, a preferred value is 22%. If the alcohol amount is made too great, not all water-soluble salts can be made to dissolve; if it is too little, not all of the hydrophobic components, in particular essential oils, will be present in clear solution. Furthermore, preservation of the essence is not assured. Thus the alcohol content is clearly defined and constant. This is also primarily of advantage in respect to the duty to declare.

Complete incineration means the oxidation of all organic components, so that only inorganic mineral substances remain behind. In general, incineration takes place at a temperature between about 300° C. to about 700° C. All organic components are burned when incineration takes place in this temperature range without the ash slagging or melting.

A suitable process is used for the exhaustive extraction of the mineral salts from the ash. Repeated maceration, digestion or Soxhlet extraction are suitable. Distilled water, for example, is suitable for this. But it can also be replaced by a portion of the second fraction or by distilled vinegar obtained by biological methods.

Depending on the extraction means employed, different purification processes for the isolated salts are usable, which can also be employed several times in succession:

For example, the dried salt extracts can again be dissolved by boiling in additional distilled water, and the miscellaneous deposits formed can again be filtered off and the solution can be dried. These steps can be repeated several times.

The dried salt extracts can also be calcined prior to renewed dissolving, in which case slagging and melting must be avoided.

In the same way, distilled wine vinegar or another distilled vinegar obtained by vinegar bacteria from alcoholic liquids, can be used in excess as a solvent. Subsequently the acid salt extracts are combined and dried, in the course of which the excess vinegar is removed. Then the salts are purified with distilled water in accordance with the above mentioned method.

Purification of the salts is necessary because the quality of the essence depends to a large extent on the purity of the soluble mineral salts. Impurities must be removed. A criterion for complete purification is whether the salts dissolve clear when boiled in distilled water.

The subsequent combination of the salts with the distillate takes place in different ways. However, a deposit forms in a few cases and must be removed. The amount of the first fraction required to dissolve the salts also depends to a great deal on the plants used. But it must be selected in such a way that all salts are completely dissolved.

A clear liquid, often colored and smelling aromatic is obtained as the end product: the spagyric essence.

I claim:

1. A method for producing spagyric essences from fresh or dried plants or parts of plants comprising:

determining a dry mass (M·T) of plant material to be used;

establishing the amount of an end product (U) based upon said dry mass of said plant material, thereby setting the amount of an intermediate product (F1) of a first fraction of a distillation and the amount of carbohydrates required for the method;

comminuting said plant material and forming a mixture of at least one fermentable carbohydrate dissolved in water, yeast and said comminuted plant material;

stirring said mixture initially to at least cover said comminuted plant material with water, and thereafter at least once a day until the comminuted plant material is completely fermented, at a temperature adapted to the yeast employed, forming a fermented mass;

distilling said fermented mass in vacuo, collecting two fractions therefrom, the first fraction containing the total amount of alcohol from the fermentation and the second fraction comprising the portion of the distillate remaining after collection of the first fraction, and forming a distillation residue;

adding alcohol to said first fraction in an amount to provide between about 10% to about 80% alcohol content in the end product (U);

drying, burning and completely incinerating said distillation residue at a temperature between about 300° C. to about 700° C., forming an ash comprising at least one soluble mineral salt;

extracting all of said at least one soluble mineral salt from said ash with a solvent producing purified salt extracts, recombining and drying said purified salt extracts while removing impurities from said extracts forming dried salts;

dissolving the dried salts in a first portion of said first fraction forming a purified salt solution, and filtering off any miscellaneous deposits which have been formed;

mixing said purified salt solution with the remaining portion of the first fraction, forming a purified salt mixture; and adding a sufficient amount of said second fraction to said purified salt mixture so that the entire amount of said purified salt mixture with said second fraction corresponds to the predetermined amount of the end product.

2. A method in accordance with claim 1, wherein said fermentable carbohydrate is sucrose.

3. A method in accordance with claim 1, wherein said fermentable carbohydrate is honey.

4. A method in accordance with claim 1, wherein said solvent is distilled water.

5. A method in accordance with claim 4, wherein the recombined and dried salt extracts are again dissolved by boiling in an additional amount of said distilled water, a miscellaneous deposit which is formed being filtered off and the solution dried.

6. A method in accordance with claim 5, the purified salt extracts are again dissolved by boiling in an additional portion of distilled water, a miscellaneous deposit which is formed being filtered off and the solution dried, said distillation, filtering and drying steps being repeated until all the purified salt extracts dissolve clearly when boiled in said distilled water, after which said clear solution is finally dried.

7. A method in accordance with claim 4, wherein the recombined and dried salt extracts are calcined without slagging or melting prior to dissolving in said distilled water.

8. A method in accordance with claim 4, wherein said distilled water used for the removal of impurities which has been extracted during salt extraction is replaced by a portion of said second fraction.

9. A method in accordance with claim 1, wherein a distilled vinegar obtained in excess from vinegar bacteria from alcoholic liquids is used;

the acid salt extracts are combined and dried in a vacuum;

the dried salts are dissolved in distilled water for the removal of a final residue of excess acetic acid and again dried in said vacuum; and said dissolving and drying steps are repeated until the distillate reacts approximately neutral.

10. A method in accordance with claim 9, wherein the dried salts, which have been freed of all excess acid, are dissolved in distilled water by boiling for the removal of impurities which were also extracted, a miscellaneous deposit which is formed being filtered off and the solution dried.

11. A method in accordance with claim 10, wherein the salts are again dissolved by boiling in distilled water, a miscellaneous deposit which is formed being filtered off and the solution dried, and said dissolving, filtering and drying steps are repeated until all the salts dissolve clearly when boiled in distilled water, after which said clear solution is finally dried.

12. A method in accordance with claim 6, wherein the recombined and dried salt extracts are calcined without slagging or melting prior to dissolving in said distilled water.

13. A method in accordance with claim 12, wherein said distilled water used for the removal of impurities which has been extracted during salt extraction is replaced by a portion of said second fraction.

* * * * *